US00PP32842P3

(12) United States Plant Patent
Sakuta et al.

(10) Patent No.: US PP32,842 P3
(45) Date of Patent: Feb. 23, 2021

(54) SHIITAKE MUSHROOM NAMED 'HOKSY 10GOKIN'

(50) Latin Name: ***Lentinula edodes* (Berk.) Pegler**
Varietal Denomination: HOKSY 10gokin

(71) Applicant: HOKUTO CORPORATION, Nagano (JP)

(72) Inventors: Genki Sakuta, Nagano (JP); Momoko Aizawa, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 314 days.

(21) Appl. No.: 15/932,645

(22) Filed: Mar. 30, 2018

(65) Prior Publication Data

US 2019/0230837 P1 Jul. 25, 2019

(30) Foreign Application Priority Data

Jan. 24, 2018 (JP) ..... PBR 32805

(51) Int. Cl.
*A01H 15/00* (2006.01)
*C12N 1/14* (2006.01)

(52) U.S. Cl.
USPC ..... Plt./394
CPC ..... *A01H 15/00* (2013.01); *C12N 1/14* (2013.01)

(58) Field of Classification Search
USPC ..... Plt./394
CPC ..... A01H 15/00
See application file for complete search history.

(56) References Cited

PUBLICATIONS

PLUTO UPOVROM Plant Variety Database Citation for 'HOKSY 10gokin' as per JP PBR 32805; Jan. 25, 2018; 1 page.*

* cited by examiner

*Primary Examiner* — Kent L Bell
(74) *Attorney, Agent, or Firm* — Taro Yaguchi

(57) ABSTRACT

The present variety of mushroom named 'HOKSY 10gokin' was cultivated by the gathering and repeated breeding of Shiitake mushrooms having dominant traits, which has good qualitative character and appearance, a white stem of high quality, and enhanced cultivation. This edible mushroom is exquisite in stability, reproducibility and uniformity when being produced.

13 Drawing Sheets

BACKGROUND OF THE INVENTION

This invention relates to a new and distinct variety of Shiitake mushroom, *Lentinula edodes* (Berk.) Pegler. This new variety named 'HOKSY 10gokin', cultivated by repeated breeding of Shiitake mushrooms having dominant traits, has a white stem of high quality and enhanced cultivation stability, and ensures presentable stability, reproducibility, and uniformity.

Shiitake mushroom is an edible mushroom having the highest production amount in Japan, which accounts for 69.1 billion yen in fresh shiitake mushrooms and 9.2 billion yen in dried shiitake mushrooms according to statistics in 2014. However, since those who engage in the production of shiitake mushrooms are mainly subsistence farmers, the supply of shiitake mushrooms is influenced by weather and the like, therefore it is difficult to stably supply shiitake mushrooms. Accordingly, there is a strong demand in the market for a stable supply of shiitake mushrooms by our company, and therefore our company has been conducting a wide variety of studies for the stable production of shiitake mushrooms. Our company has developed a 'HOKSY 8gokin' mushroom with a resistance to lamella breakage, and which has few malformations thus far. Nevertheless, the 'HOKSY 8gokin' mushroom had problems in terms of quality, such as coloring of the stem.

As a result of continuing breed improvement by cross breeding so as to improve the above problem and further enhance cultivation stability, a 'HOKSY 10gokin' mushroom was developed with a white stem of high quality, as compared to the 'HOKSY 8gokin' mushroom, and had higher cultivation stability than the 'HOKSY 8gokin' mushroom.

SUMMARY OF THE INVENTION

The present invention is a new and distinct variety of mushroom characterized particularly by its good qualitative character and appearance, a white stem of high quality, and enhanced cultivation, which can be cultivated by gathering and repeated breeding of fungal strains having dominant traits and is exquisite in stability, reproducibility and uniformity when being produced. This novel and distinct variety of mushroom is identified as 'HOKSY 10gokin'.

DETAILED DESCRIPTION OF THE INVENTION

'HOKSY 10gokin' mushroom was discovered in Nagano-shi, Nagano, Japan where the temperature, humidity and carbon dioxide concentration are controlled. 'HOKSY 10gokin' was asexually reproduced by inoculating on a potato dextrose agar with hyphae and incubating in a culture room set at 25° C. The history of the 'HOKSY 10gokin' mushroom in terms of improvement period and the like are set forth in the following chronological list of each stage of variety improvement:

March 2009: Cultivation of 'MH009092' strain.

March 2014: Cultivation of 'MH009106' strain.

June 2017: 'MH009092' and 'MH009106' strains were crossed and an excellent strain 'MH009107' was selected.

January 2018: Growing test was repeatedly conducted on 'MH009107' and since distinguishability, stability and uniformity were confirmed, the strain was named 'HOKSY 10gokin' and cultivation was completed. Applied for registration of a new variety to the Ministry of Agriculture, Forestry and Fisheries of Japan. Registered the Application No. 32805 on Jan. 24, 2018.

In physiological characteristics, the amount of aerial hyphae development when growing hyphae on an agar medium is smaller than that of the parent varieties 'HOKSY 8gokin', and the Density of hyphae is lower than that of the parent varieties 'HOKSY 3gokin' and 'HOKSY 8gokin'. In morphological characteristics, the shape of the gill is different from that of 'HOKSY 3gokin'. Also, the stipe length is shorter than that of 'HOKSY 8gokin'.

Figure 1:
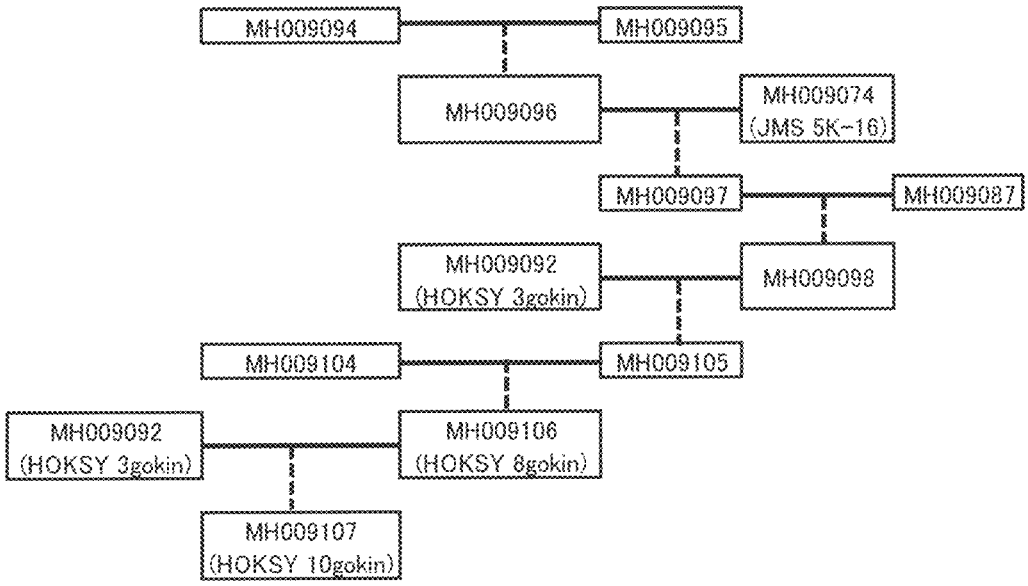
FIG. 1 shows a phylogenetic tree illustrating the antecedents of 'HOKSY 10gokin', 'HOKSY 3gokin' and 'JMS 5K-16' strains.
Figure 2B:
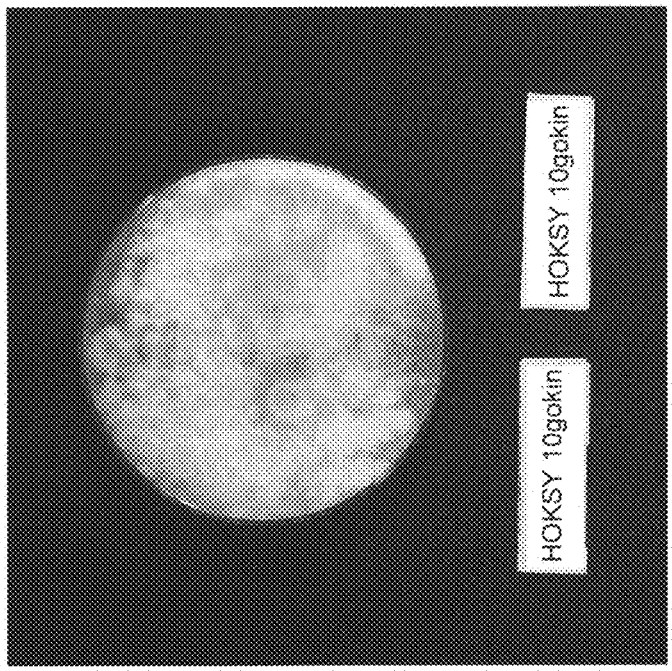
FIGS. 2A and 2B respectively show front and back images of a dual-culture of 'HOKSY 10gokin' colony.
Figure 2A:
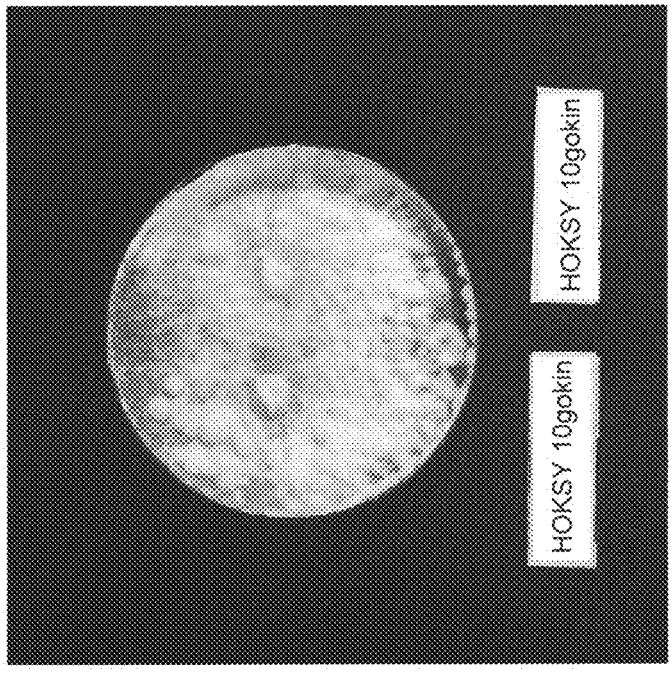
Figure 3B:
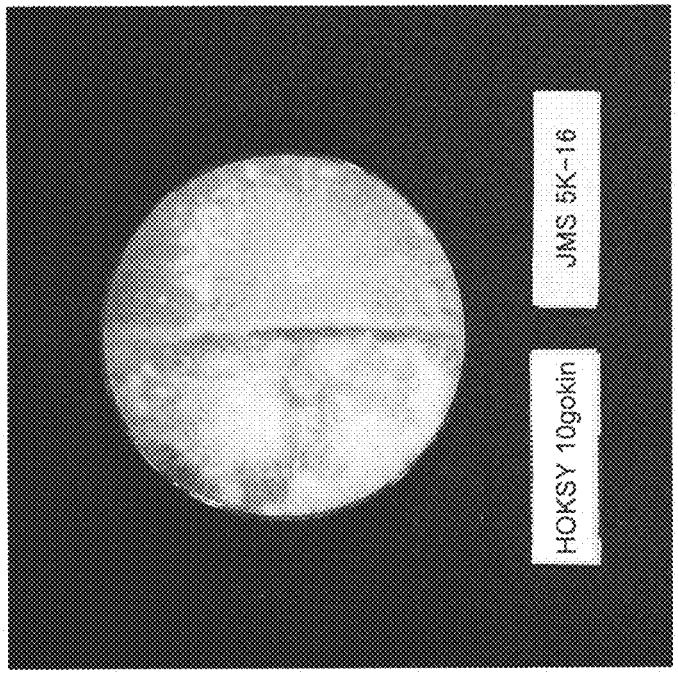
FIGS. 3A and 3B respectively show front and back images of a dual-culture of 'HOKSY 10gokin' and 'JMS 5K-16' strains.
Figure 3A:
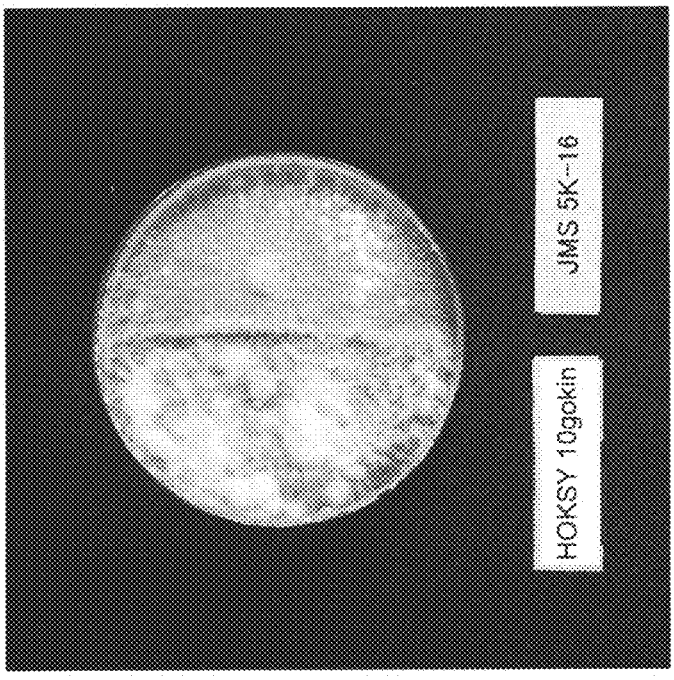
Figure 4B:
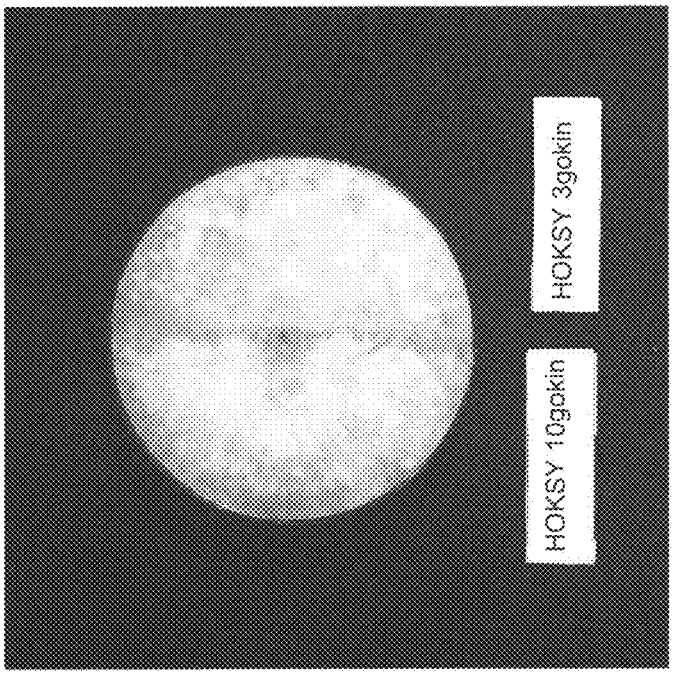
FIGS. 4A and 4B respectively show front and back images of a dual-culture of 'HOKSY 10gokin' and 'HOKSY 3gokin' strains.
Figure 4A:
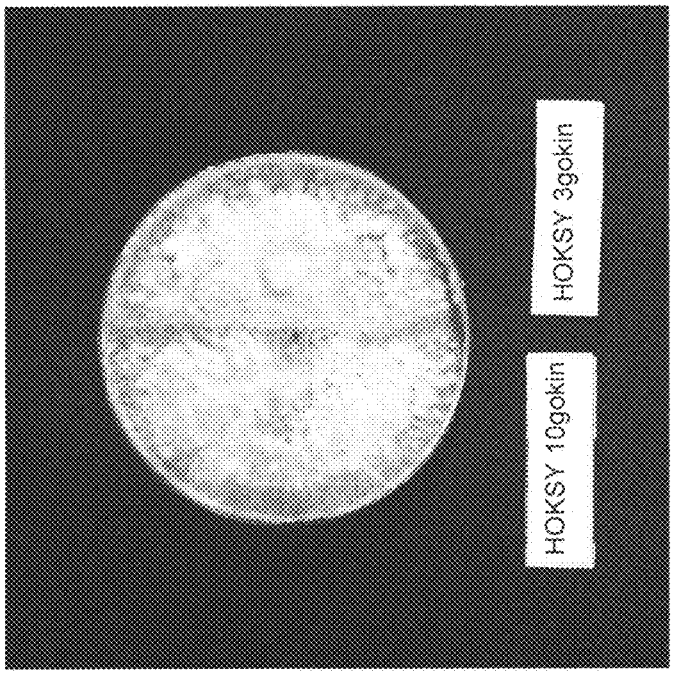
Figure 5:
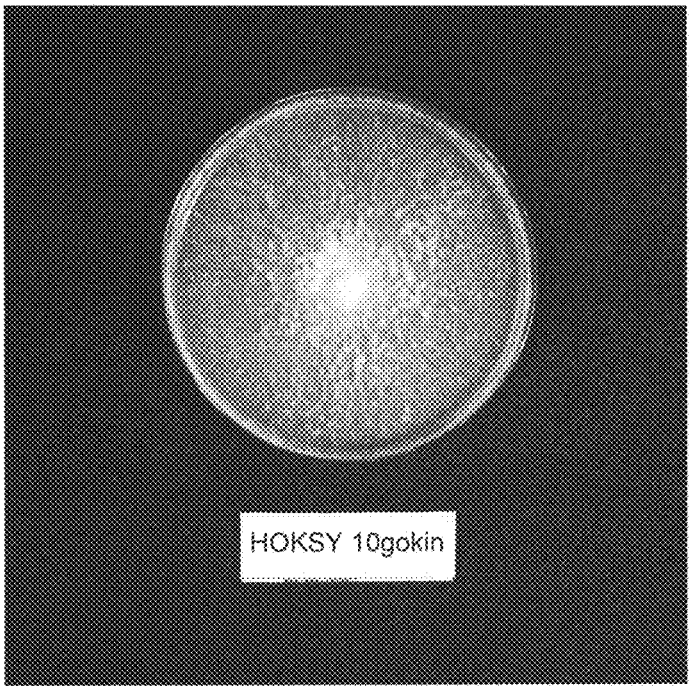
FIG. 5 shows an image of the surface of fungal flora of 'HOKSY 10gokin'.
Figure 6:
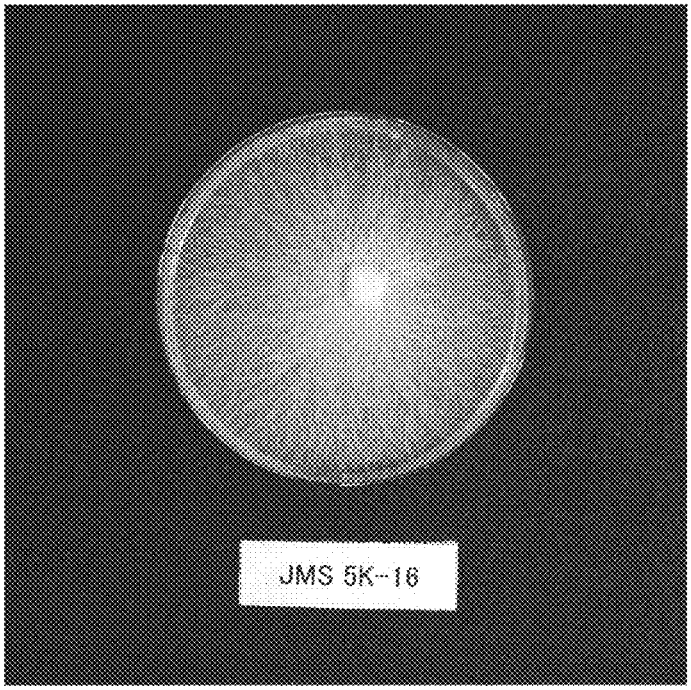
FIG. 6 shows an image of the surface of fungal flora of 'JMS 5K-16'.
Figure 7:
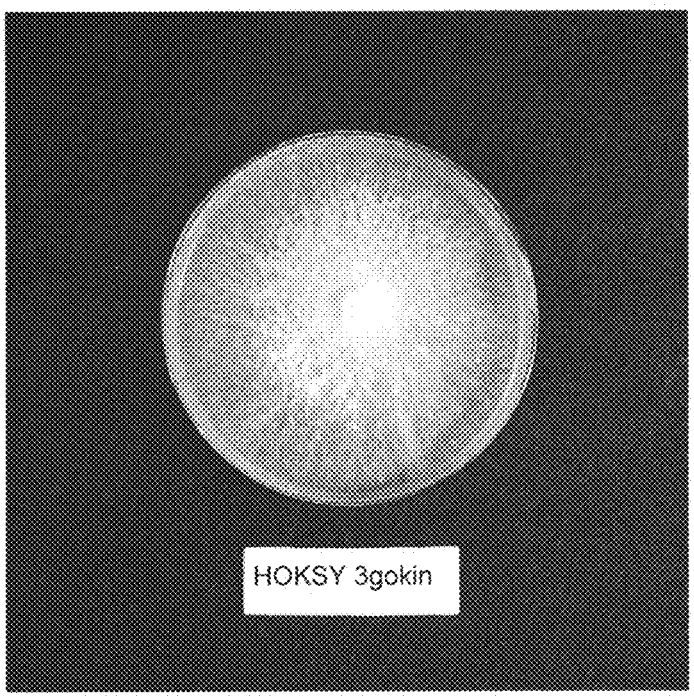
FIG. 7 shows an image of the surface of fungal flora of 'HOKSY 3gokin'.
Figure 8:
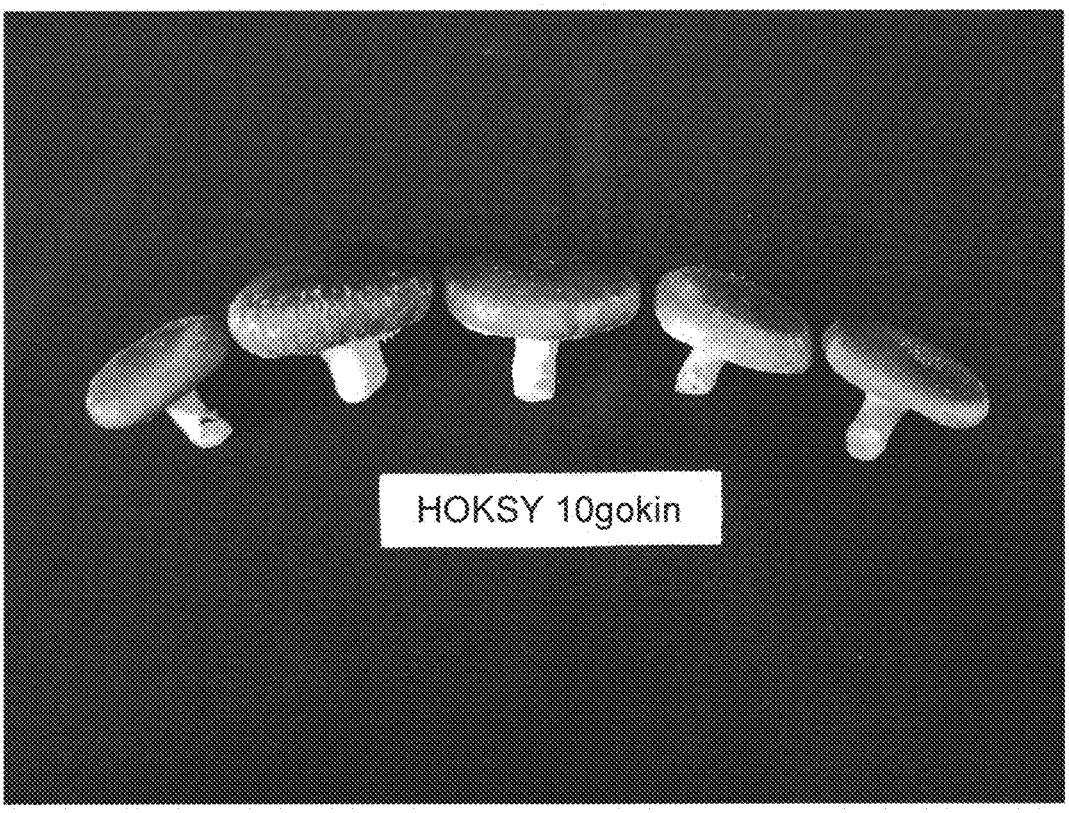
FIG. 8 shows an image of fruit bodies of 'HOKSY 10gokin'.
Figure 9:
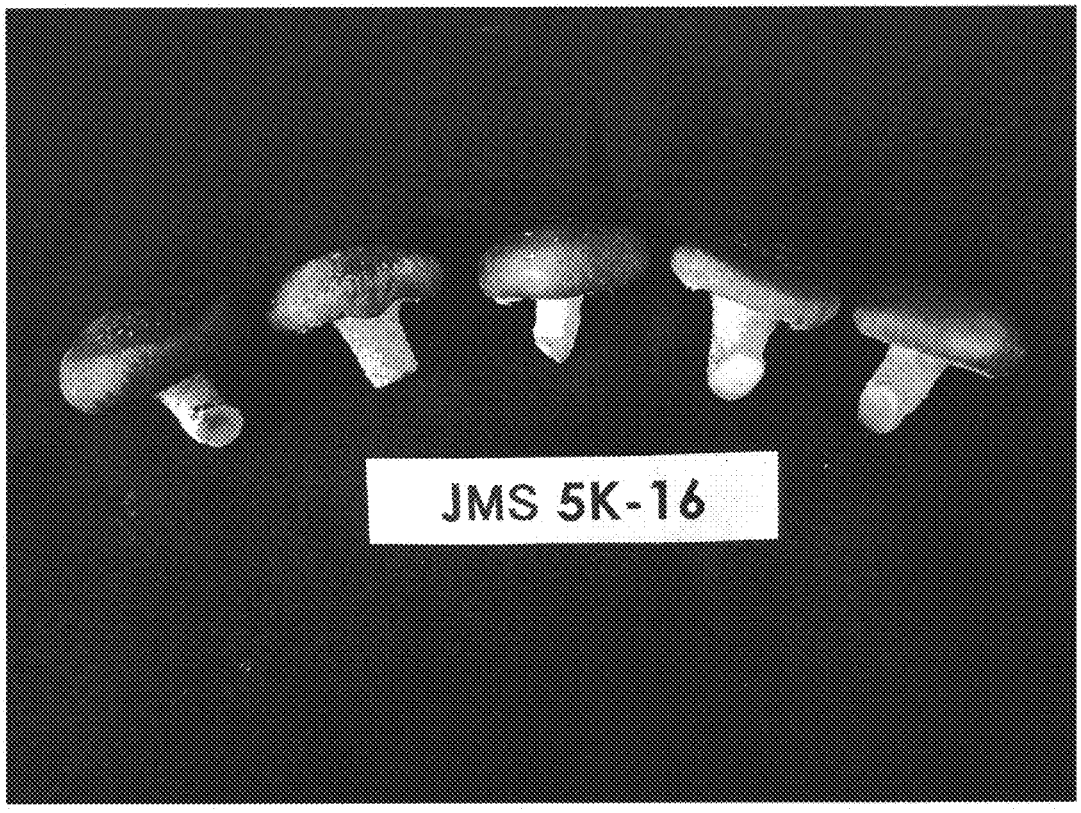
FIG. 9 shows an image of a fruit body of 'JMS 5K-16'.
Figure 10:
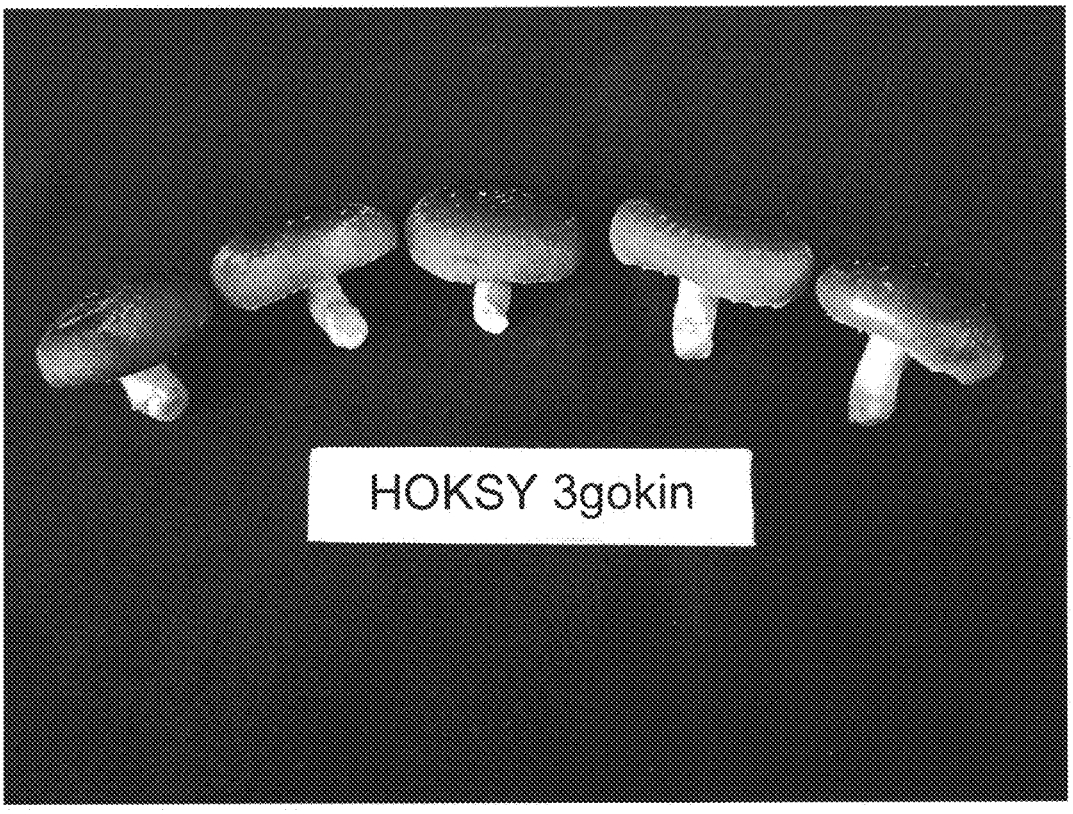
FIG. 10 shows an image of a fruit body of 'HOKSY 3gokin'.
Figure 11A:
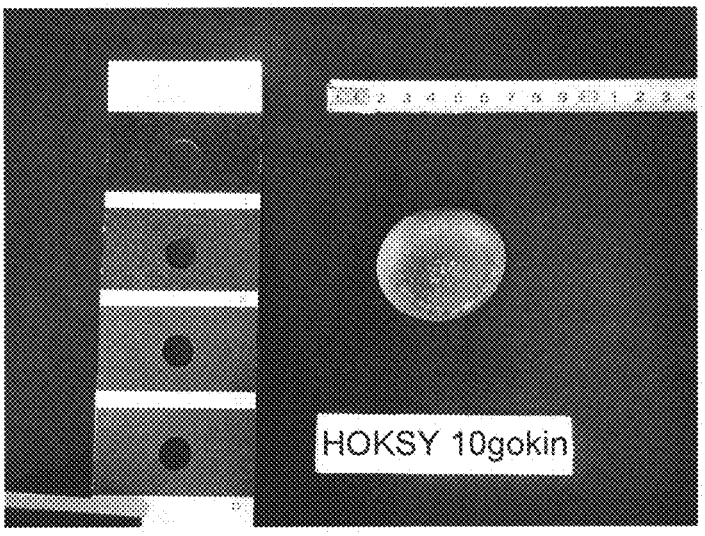
FIGS. 11A, 11B, and 11C respectively show top, underside, and cross-sectional images of a fruit body of 'HOKSY 10gokin'.
Figure 11B:
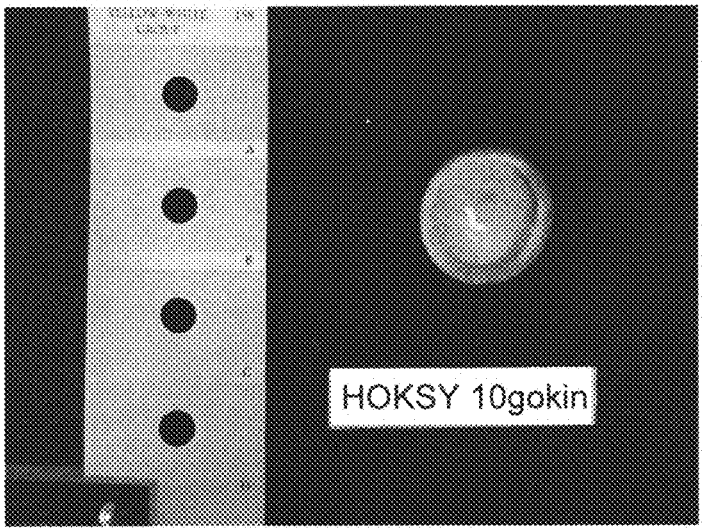
Figure 11C:
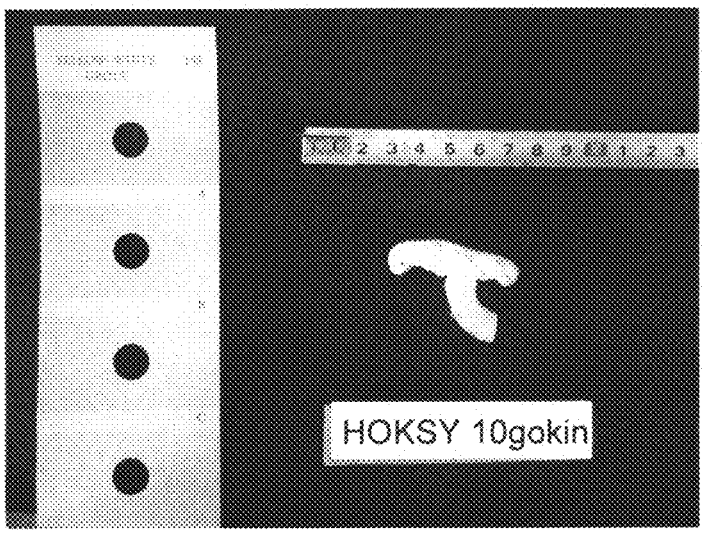
Figure 12A:
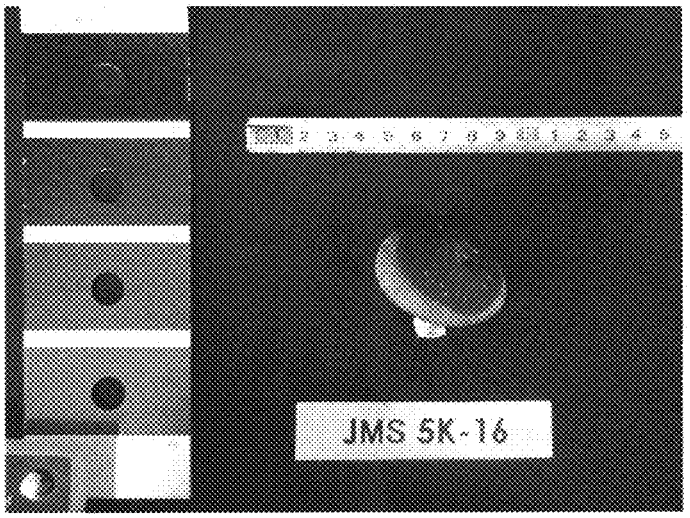
FIGS. 12A, 12B, and 12C respectively show top, underside, and cross-sectional images of a fruit body of 'JMS 5K-16'.
Figure 12B:
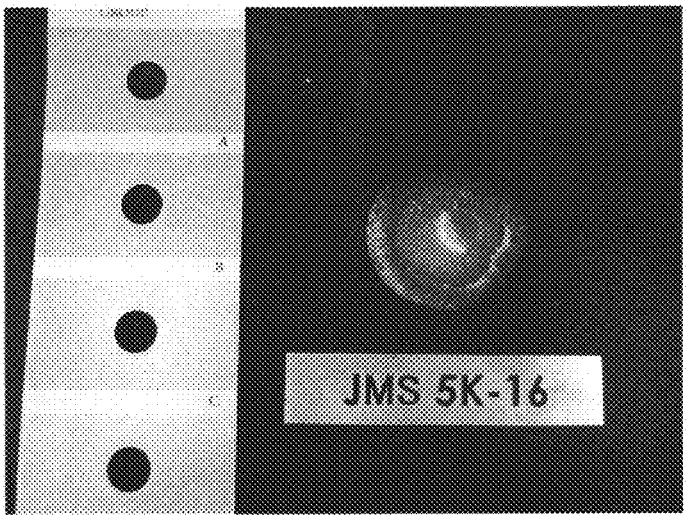
Figure 12C:
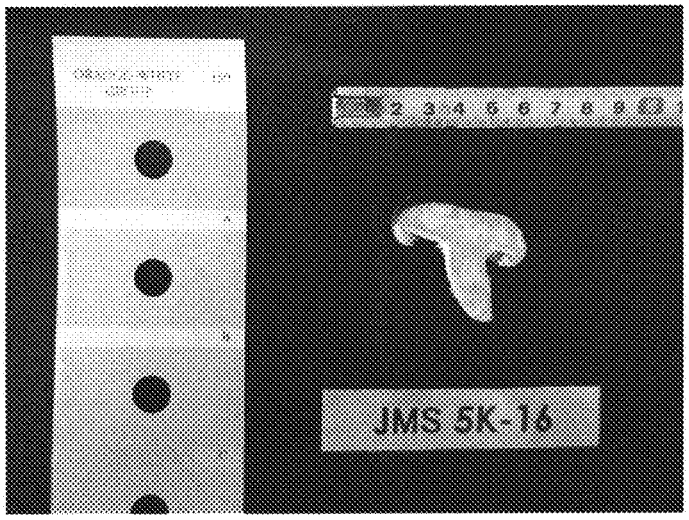
Figure 13A:
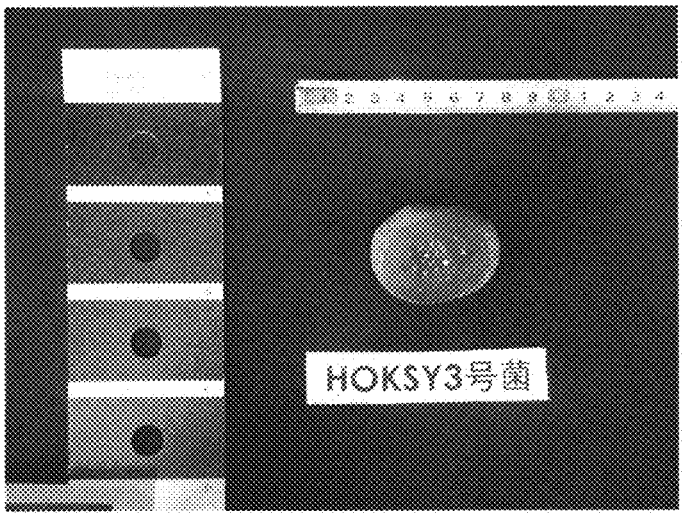
FIGS. 13A, 13B, and 13C respectively show top, underside, and cross-sectional images of a fruit body of 'HOKSY 3gokin'.
Figure 13B:
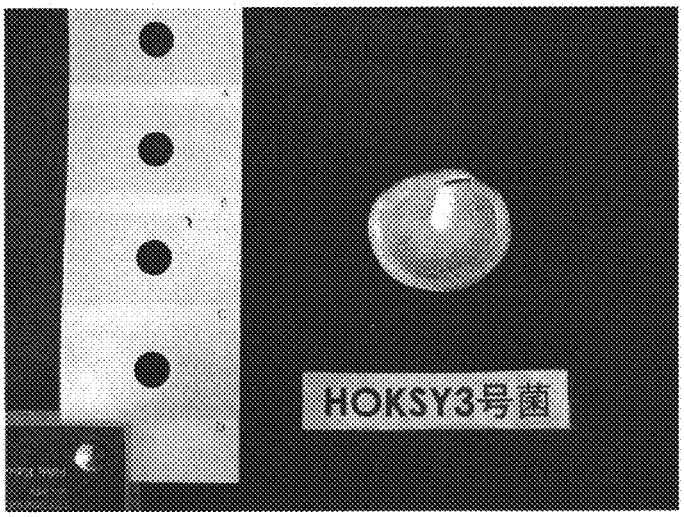
Figure 13C:
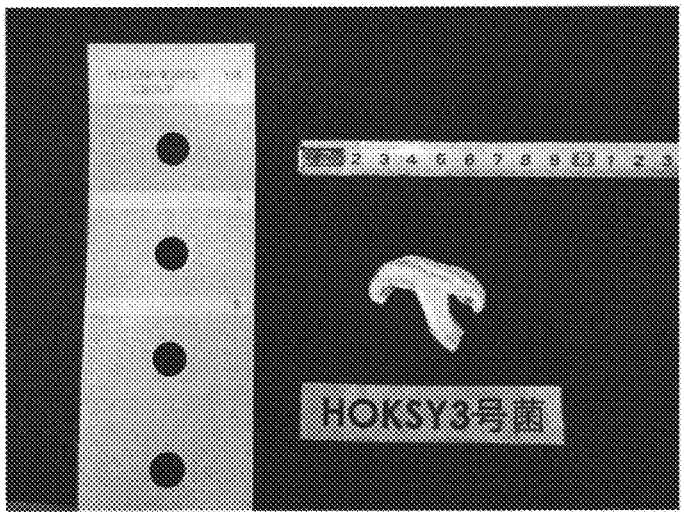

The above crossing is summarized in the phylogenetic tree illustrated in FIG. 1.

The 'HOKSY 10gokin' mushroom has the following characteristics: a white stem of high quality, and enhanced cultivation.

(1) Comparison with Existing Variety by Dual Culture

Dual culture was performed for the 'HOKSY 10gokin' mushroom and a similar variety so as to examine whether or not a zone line is formed.

Study Method:

As an examination method, a potato dextrose agar medium was used, and the 'HOKSY 10gokin' mushroom and the similar variety were inoculated thereon face to face at an interval of 3 cm, and then culture was performed at 25° C. for 28 days to examine whether or not a zone line was formed.

Strain Used:

'HOKSY 10gokin': Present variety

'JMS 5K-16': Variety similar to the present variety

'HOKSY 3gokin': Variety similar to the present variety

Results:

No zone line was formed in the dual culture of 'HOKSY 10gokin' strains (Table 1), while a zone line was formed between the 'HOKSY 10gokin', and 'JMS 5K-16' and 'HOKSY 3gokin' strains (Table 1). This clearly shows that the present mushroom is a new variety.

TABLE 1

Results of dual culture

| | Similar variety 'JMS 5K-16' | Similar variety 'HOKSY 3gokin' | Present variety 'HOKSY 10gokin' |
|---|---|---|---|
| 'HOKSY 10 gokin' | + | + | – |

+ is present and – is absent.

(2) Growth Characteristics of 'HOKSY 10gokin'

(2)-1 Temperature Adaptation of Hyphae

Study Method:

After inoculating an agar piece of the 'HOKSY 10gokin' having a diameter of 5 mm and an agar piece of the similar variety having a diameter of 5 mm on a potato dextrose agar medium, preculture was performed at 25° C. for 4 days so as to make the regeneration of hyphae equal (about 10 mm in diameter), and then culture was performed for 7 days at intervals of 5° C. between 5° C. and 30° C. An average daily hyphae growth rate was calculated based on a hyphae growth rate for seven days of the culture.

Results:

There was no significant difference in hyphae elongation rate between the 'HOKSY 10gokin' mushroom and that of the similar varieties at each temperature zone (Table 2).

(2)-2 Comparison in the Formation of Hyphae Tunic, Aerial Hyphae, Hyphae Density and Tinting of the Surface of Fungal Flora Study Method:

After inoculating an agar piece of the 'HOKSY 10gokin' having a diameter of 5 mm and an agar piece of the similar variety having a diameter of 5 mm on a potato dextrose agar medium, culture was performed at 25° C. for 14 days. For these two strains, comparative observation was performed with regard to hyphae tunic, aerial hyphae and tinting of the surface of fungal flora.

Results:

The formation of hyphae tunic was confirmed in the 'HOKSY 10gokin' mushroom, while it was not confirmed in the similar variety 'JMS 5K-16' (Table 2). With regard to aerial hyphae, there was no difference between the present variety and the similar varieties (Table 2). Regarding hyphae density, while for the 'HOKSY 10gokin' mushroom it is medium, it was dense in similar variety 'HOKSY 3gokin'

(Table 2). Tinting of the surface of fungal flora was observed in the 'HOKSY 10gokin' mushroom, while it was not confirmed in the similar variety 'JMS 5K-16' (Table 2).

(3) Morphological Characteristics of the 'HOKSY 10gokin' Mushroom in a Cultivation Example Cultivation Method:

Mushroom bed bag: A mushroom bed bag made of polyethylene (117 mm×230 mm, 35φ) was used.

Culture medium: Sawdust, rice bran and wheat bran were mixed at the dry weight ratio of 8:1:1, and the water content was adjusted to 63%. The amount of a medium filled was 1.5 kg per bag, and high-pressure sterilization was performed.

Starter culture: About 20 mL of sawdust starter cultures per bottle was inoculated.

Culture: Culture was performed at 20° C. for 85 days at 60-70% moisture.

Growth: After completing the culture, the mushroom bed was taken out of the bag and washed with water, and then mushrooms were grown at 13-14° C., at 90% moisture or higher at a $CO_2$ concentration of 1,000 ppm or lower. An immersion method was used as the generation method on the second time and thereafter.

Cultivation Results:

Table 2 shows the characteristics of the 'HOKSY 10gokin' and specific difference in characteristics as compared with the similar variety when culture was performed under the abovementioned conditions.

Also, the whole, top, underside, and cross-sectional images of the respective fruit bodies have also been attached. (Refer to FIGS. 8 to 13).

TABLE 2

Fungus characteristics Table of *Lentinula edodes* (Berk.) Pegler of Recording and Registration

| | Present variety 'HOKSY 10gokin' | Similar variety 'JMS 5K-16' | Similar variety 'HOKSY 3gokin' |
|---|---|---|---|
| Genetic property | | | |
| Formation of zone line | + | + | + |
| Physiological property | | | |
| Formation of hyphae tunic | + | − | + |
| Aerial hyphae development | medium | medium | medium |
| Density of hyphae | medium | medium | dense |
| Tinting of surface of fungal flora | + | − | + |
| Temperature adaptability | | | |
| Tolerance for High or Low Temperature | | | |
| Optimal temperature for hyphal growth (° C.) | 25 | 25 | 25 |
| Hyphal growth rate at each temperature (mm/day) | | | |
| 5° C. | 0.36 | 0.47 | 0.45 |
| 10° C. | 1.47 | 1.42 | 1.40 |
| 15° C. | 2.36 | 2.59 | 2.63 |
| 20° C. | 4.31 | 4.42 | 4.48 |
| 25° C. | 5.13 | 5.19 | 5.34 |
| 30° C. | 2.96 | 3.45 | 3.10 |

TABLE 2-continued

Fungus characteristics Table of *Lentinula edodes* (Berk.) Pegler of Recording and Registration

| | Present variety 'HOKSY 10gokin' | Similar variety 'JMS 5K-16' | Similar variety 'HOKSY 3gokin' |
|---|---|---|---|
| Morphological property | | | |
| Cap | | | |
| Shape of top view | round | round | round |
| Shape of vertical cross section | flat | flat | flat |
| Fleshy type | quarter circle shape | quarter circle shape | quarter circle shape |
| Diameter (mm) | 46.31 | 38.83 | 40.01 |
| Main color of apex | brown [RHS:200C] | brown [RHS:200C] | brown [RHS:200C] |
| Thickness (mm) | 11.80 | 11.70 | 12.56 |
| Hardness | medium | medium | medium |
| Distribution of scales | periphery | periphery | periphery |
| Size of scales | medium | medium | medium |
| Coloring of scales | + [RHS: 158B] | + [RHS: 159B] | + [RHS: 158B] |
| Gill | | | |
| Shape | wedge shape | rectangular triangle shape | rectangular triangle shape |
| Arrangement | ripple or crinkle | straight | ripple or crinkle |
| Width (mm) | 2.45 | 1.04 | 2.08 |
| Density | medium | medium | medium |
| Color | cream [RHS: 158B] | cream [RHS: 159B] | cream [RHS: 158B] |
| Stipe | | | |
| Shape | head portion | head portion | head portion |
| Length (mm) | 30.05 | 41.86 | 34.17 |
| Ratio of cap diameter/stipe length | 1.55 | 0.95 | 1.19 |
| Thickness (mm) | 10.12 | 13.60 | 10.18 |
| Ratio of cap diameter/stipe thickness | 4.63 | 2.92 | 3.99 |
| Tinting of surface | + [RHS: 159B] | + [RHS: 159B] | + [RHS: 159B] |
| Presence of fluff | + | + | + |
| Tinting of fluff | + [RHS: 159B] | + [RHS: 159B] | + [RHS: 159B] |
| Hardness | hard | hard | hard |
| Cultural property | | | |
| Period from inoculation to fruit induction (day) | 70 | 70 | 70 |
| Period from fruit induction to harvest (day) | 10.0 | 10.0 | 10.0 |
| Type of fruiting | concentrated | concentrated | concentrated |
| Soaking treatment | suitable | suitable | suitable |
| Temperature of soaking yield (° C.) | 14 | 14 | 14 |
| Method of secondary fruiting | use jointly | use jointly | use jointly |
| Fruiting temperature (° C.) | 14 | 14 | 14 |
| Adaptability of culture medium | broad leaved | broad leaved | broad leaved |
| Ratio of dry weight fruit body (%) | 10.4 | 10.3 | 10.4 |

TABLE 2-continued

Fungus characteristics Table of *Lentinula edodes* (Berk.) Pegler of Recording and Registration

| | Present variety 'HOKSY 10gokin' | Similar variety 'JMS 5K-16' | Similar variety 'HOKSY 3gokin' |
|---|---|---|---|
| Average of 1 dry weight fruit body (g/piece) | 1.9 | 2.0 | 1.9 |
| Yield | | | |
| Yield of sawdust medium 100 kg (kg) | 2.72 | 3.08 | 3.09 |
| Ratio of every month yield (%) | | | |
| 1st month | 60.9 | 55.5 | 57.1 |
| 2nd month | 14.4 | 10.5 | 13.8 |
| 3rd month | 15.1 | 23.8 | 14.6 |
| 4th month | 9.6 | 12.5 | 12.2 |

* The employed color chart is R.H.S Colour Chart, 2007, Fifth edition, prescribed by Royal Horticultural Society, England.

What is claimed is:

1. A new, distinct variety of Shiitake mushroom as substantially illustrated and described in the specification.

* * * * *